United States Patent [19]

Spohn

[11] Patent Number: 4,978,760

[45] Date of Patent: Dec. 18, 1990

[54] PREPARATION OF HALOGEN SUBSTITUTED PHTHALIC ANHYDRIDE

[75] Inventor: Ronald F. Spohn, Williamsville, N.Y.

[73] Assignee: Occidental Chemical Corporation, Niagara Falls, N.Y.

[21] Appl. No.: 160,035

[22] Filed: Feb. 24, 1988

[51] Int. Cl.$^5$ ............................................. C07D 307/89
[52] U.S. Cl. .................... 549/246; 549/240; 549/247
[58] Field of Search ......................... 549/240, 246, 247

[56] References Cited

U.S. PATENT DOCUMENTS

| | | | |
|---|---|---|---|
| 4,560,772 | 12/1985 | Telschow et al. | 549/240 |
| 4,560,773 | 12/1985 | Telschow | 549/240 |
| 4,709,056 | 11/1987 | Cotter et al. | 549/240 |

OTHER PUBLICATIONS

Ohkatsu et al, J. Japan Petrol. Inst., vol. 22 (1979), pp. 164–169.
Bergmann, J.A.C.S., vol. 64 (1942) pp. 176–177.
Russian Chemical Reviews, Nov. 1963, pp. 571–589.
Hampel et al, Glossary of Chemical Terms, 2nd Ed., Van Nostrand (1982) pp. 5 & 6.

*Primary Examiner*—Richard L. Raymond
*Attorney, Agent, or Firm*—James F. Tao; Arthur S. Cookfair

[57] ABSTRACT

A process for the preparation of halogen substituted phthalic anhydrides of the formula:

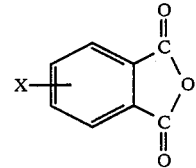

wherein x is a halogen, by the reaction of a halogen substituted tetrahydrophthalic phthalic anhydride of the formula

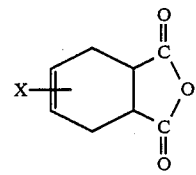

or a geminal dihalogen substituted hexahydrophthalic anhydride of the formula

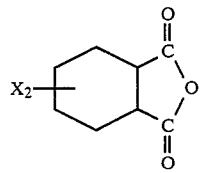

in a vapor or liquid phase while mixed with an air flow and an activated carbon catalyst at an elevated temperature.

14 Claims, No Drawings

PREPARATION OF HALOGEN SUBSTITUTED PHTHALIC ANHYDRIDE

BACKGROUND OF THE INVENTION

This invention is concerned with the process for the aromatization of a cyclic compound to form a fully aromatic ring structure. More particularly, it relates to a process for producing a halogen substituted phthalic anhydride from a halogen substituted tetrahydrophthalic anhydride or from a dihalogen substituted hexahydrophthalic anhydride.

Substituted phthalic anhydrides are valuable raw materials for the synthesis of useful products. These anhydrides are utilized as intermediates in the synthesis of organic polymers, dyes, plasticizers and in other uses.

Procedures are known for preparing substituted phthalic anhydrides. U.S. Pat. No. 4,560,772 discloses the reaction of 4-methyltetrahydrophthalic anhydride with excess sulfur and a catalytic amount of zinc oxide and 2-mercaptobenzothiazole to produce 4-methylphthalic anhydride and hydrogen sulfide.

U.S. Pat. No. 4,560,773 discloses a similar reaction between the electron rich 4-methyl-tetrahydrophthalic anhydride and bromine in the presence of a catalytic amount of an acid acceptor such as dimethylformamide or pyridine in the liquid phase.

U.S. Pat. No. 4,709,056 discloses the dehydrohalogenation of dihalohexahydrophthalic anhydrides through the use of a basic alumina catalyst in a liquid phase to produce 4-fluoro-1,2,3,6-tetrahydrophthalic anhydride.

Ohkatsu et al., *J. Japan Petrol. Inst.*, 22, 164–9 (1979) discloses the dehydrogenation of hydrocarbons using an activated carbon bed to produce the corresponding olefins. The mechanism of the reaction using cyclohexane and cyclohexene were studied using a pressure flow technique.

Bergmann *J. Amer. Chem. Soc.* 64, 176 (1942) discloses the aromatization of tetrahydrophthalic anhydride products of Diels-Alder reactions. The author discloses that dehydrogenation occurs when the tetrahydrophthalic anhydride product is boiled in nitrobenzene. However, it is further disclosed that dehydrogenation does not occur when p-bromonitrobenzene, p-chloronitrobenzene, or m-dinitrobenzene in xylene is employed. Moreover, it has been found that when the dihalohexahydrophthalic anhydrides of this publication are dehydrogenated in nitrobenzene, a portion of the nitrobenzene is reduced to aniline. The aniline reacts with the anhydride group of either the starting material or product to form imides and thus lower the yield of desired product.

Skvarchenko et al, *Obshchei Khimiil*, Vol. 30, No. 11, pp 3535–3541 (1960) disclose the aromatization of chlorosubstituted tetrahydrophthalic anhydride by heating with phosphorus pentoxide. In the aromatization process described however, decarboxylation also occurs with the formation of the corresponding chlorosubstituted benzene compound. The preparation of tetrahydrophthalic acids and anhydrides and various methods for dehydrogenation and aromatization thereof are reviewed by Skvarchenko in *Russian Chemical Reviews*. Nov. 1963, pp. 571–589.

The aromatization of organic compounds has been shown by various techniques and the use of special catalysts seem to control the satisfactory conversion at useful product yields and conversion times. This study was undertaken to determine if a vapor state aromatization of halogen substituted materials such as halogenated tetrahydrophthalic anhydrides or geminal dihalogen hexahydrophthalic anhydrides could be converted to a monohalogenated phthalic anhydride at adequate yields and within a reasonable time.

Experimentation has shown that the use of air flow and a heated activated carbon surface can aromatize halogenated saturated phthalic anhydrides to halogenated aromatic phthalic anhydrides, and is the subject of this application.

It is the object of the present invention to provide novel intermediate compounds which are useful and provide a commercially attractive synthetic route.

SUMMARY OF THE INVENTION

This invention relates to a method for the preparation of a halogen substituted phthalic anhydride from a halogen substituted tetrahydrophthalic anhydride or from a geminal dihalogen substituted hexahydrophthalic anhydride.

The reaction is conducted in the vapor phase by the passage of the vaporized halogen substituted tetrahydrophthalic anhydride through a reaction zone at elevated temperatures in the presence of an activated charcoal as catalyst. The vaporized material is assisted through the reaction zone with a steady flow of air. The temperature of the reaction zone is in the range of 200°–400° C. or preferably 200°–325° C.

The starting material need not be vaporized before entry into the reactor, but may be dissolved in a volatile solvent and the solvent solution passed into the reactor where vaporization occurs and is then passed through the activated carbon packed section of the reaction tube.

This reaction may also be conducted in the liquid phase, wherein the starting material is optionally dissolved in a solvent, in the presence of activated carbon and air at a temperature of 200°–300° C. or preferably 200°–250° C. A typical solvent is 1,2,4-trichlorobenzene or any solvent that is stable in the reaction temperature range.

A typical example of the reaction uses 4-chlorotetrahydrophthalic anhydride as a starting material and yields 4-chlorophthalic anhydride as the end product.

DETAILED DESCRIPTION OF THE INVENTION

This invention is concerned with the aromatization of a cyclic compound to form a fully aromatized ring and specifically to convert a halogen substituted tetrahydrophthalic anhydride into a halogen substituted phthalic anhydride. The aromatization reaction occurs in the vapor phase by the passage through reaction zone in the presence of activated carbon as a catalyst, using an air flow to assist in the passage of the reactant through the heated zone.

The air flow is controlled for several reasons: to prevent the ignition of the activated carbon catalyst; to force the active components through the reactor tube; and to remove the adsorbed hydrogen from the surfaces of the carbon. The oxygen in the air will unite with the hydrogen liberated and react to form water.

The starting material employed in this invention can be prepared by various known preparation methods, and many such compounds are commercially available. Diels-Alder addition reactions of a maleic anhydride with a conjugated diene is a typical reaction and produces such an anhydride with a partically saturated six membered ring. Depending upon the desired product, the diene and/or the maleic anhydride can contain substituents to provide the starting material for this invention. The following halogen substituted partially saturated phthalic anhydrides can be employed but are not limited to the following: 4-chloro-1,2,3,6-tetrahydrophthalic anhydride; 4-fluoro-1,2,3,6-tetrahydrophthalic anhydride; 4-bromo-1,2,3,6-tetrahydrophthalic anhydride; 4-chloro-1,2,5,6-tetrahydrophthalic anhydride; 4-fluoro-1,2,5,6-tetrahydrophthalic anhydride, 4-bromo-1,2,5,6-tetrahydrophthalic anhydride; 4,4-difluorohexahydrophthalic anhydride; 4,4-dichlorohexahydrophthalic anhydride; 4,4-dibromohexahydrophthalic anhydride; 3-chloro-1,2,5,6-tetrahydrophthalic anhydride; 3-fluoro-1,2,5,6-tetrahydrophthalic anhydride; 3-bromo-1,2,5,6-tetrahydrophthalic anhydride; 3,3-difluorohexahydrophthalic anhydride; 3,3-dichlorohexahydrophthalic anhydride; 3,3-dibromohexahydrophthalic anhydride; the corresponding iodide derivatives can also be included.

The catalyst effective in this process may be any commercially available activated charcoal. Conveniently used forms are granular activated charcoals such as those available from Calgon Corporation, Pittsburgh, PA, designated Calgon F-300 (coal based); Calgon PCB (coconut-shell based); Calgon APC (coal based); Norit MRX (peat based) and Norit KB activated carbon (peat based) available from American Norit Company, Jacksonville, FL; Carborundum GAC 40; Aldrich activated Carbon (Cat. No. 24,223-3) available from Aldrich Chemical Co., Milwaukee, WI, Nuchar WV-B manufactured by Westvaco Corp. or similar granular forms suitable for passing organic vapors through them. Alternatively, powdered forms of activated charcoal may be used.

The aromatization reaction is conducted in the vapor phase. The reaction is conducted using a metallic tube, preferably of a nickel base and is heated to a temperature to assist in the vaporization of the components. A portion of the tube contains activated carbon. The procedure involved heating for example 4-chlorotetrahydrophthalic anhydride until it melts and then with the aid of a pump, was pumped into the reaction tube, air was also passed into the heated reaction tube. The two gases mixed as they passed through the tube entering the region of the tube wherein the activated charcoal was placed. The reaction occurred in the region and the products were vented from the tube into a cooler container which allowed the collection of the 4-chlorophthalic anhydride and the H2O produced was allowed to escape or be trapped in an aqueous media.

The reaction may also be conducted by dissolving the starting material in a volatile solvent and passing the solution into the heated reactor and allowing vaporization to occur therein, before passage into the section of the reactor containing the activated carbon.

The entry of air into the reactor may be undertaken in several ways, by using a pressurized flow into the entry end of the reactor tube, or by applying a vacuum to the outlet of the collection and/or trap units. Either method is satisfactory for the movement of the gases through the reactor.

When a solution of the starting material is employed, a solvent such as toluene or ethyl acetate is used, and the solution is fed into the reactor by a pump or by gravity where the elevated temperature of the reactor and the air flowing therethrough vaporizes the solvent solution for passage into the reaction zone.

The mechanism of the reaction described above is believed to involve the removal of hydrogens from the saturated ring which unite with the oxygen in the air flow to create water, for example:

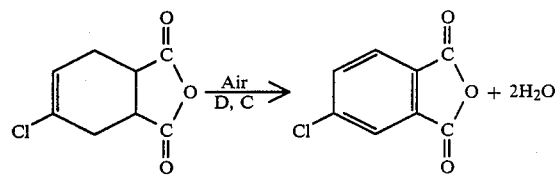

If a geminal dihalogen substitutent is used as the starting material, a halogen acid and water would be produced as by-products as illustrated by:

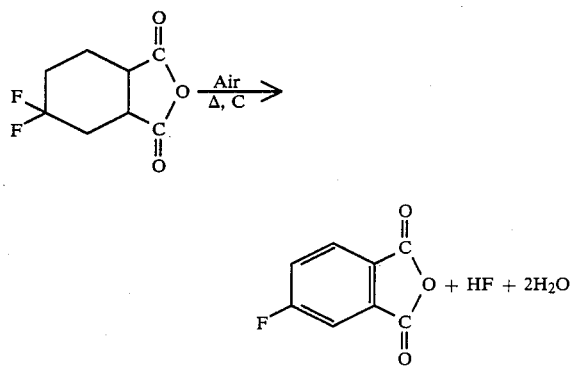

EXAMPLE I

A U shaped nickel reactor tube, ½ inch 1D, each leg being 6 inches long, was wrapped with heating tapes and into the outlet end of the tube was packed 12.75 grams of activated carbon (Nuchar WV-B manufactured by Westvaco Corp.) and placed within the carbon particles are thermocouples to measure the temperature. At the feed end of the reaction tube are two openings, one, for the air feed and the second, for the raw material feed. To the outlet of the reactor is placed a series of receivers and traps to collect the product and entrap the acid produced. A quantity of 4,4-difluorohexahydrophthalic anhydride was dissolved in toluene and was transferred, in a steady flow, to the inlet on the reactor tube. The pressure was reduced to 150 mm Hg to prevent back flow of gases. The raw material solution was fed at the rate of 1.1 ml/min to the reactor, the reactor temperatures was 350° C., air flow was 122 ml/min. The reaction was conducted under these temperatures and conditions and a product of 4fluorophthalic anhydride was obtained at a 52% yield.

EXAMPLE II

The same equipment and feed rates as described in Example I was employed, except the starting material was 4-chlorotetrahydrophthalic anhydride was used. This material was dissolved in toluene using a 20% solution. The product 4-chlorophthalic anhydride was recovered at a 31% yield.

EXAMPLE III

Into a 3 necked round bottom flask is placed 49.47 grams of 4-chlorotetrahydrophthalic anhydride, 20.26 g activated carbon (NORIT CA-1) and 200 ml of 1,2,4-trichlorobenzene. The flask is fitted with an air inlet tube, a stirrer, and an addition funnel-condenser to collect water and allow the reflux to return to the flask. The flask was heated and raised to 230° C. with a constant flow of air. The reaction was conducted for eight hours. The carbon was removed by filtration and washed. The contents was concentrated under vacuum and analysis confirmed a yield of 67% 4-chlorophthalic anhydride and 4% of unreacted starting material.

While the invention has been described in connection with specific embodiments thereof, it will be understood that it is capable of further modification, and this application is intended to cover any variation, uses, or adaptations of the invention following, in general, the principles of the invention and including such departures from the present disclosure as come within known or customary practice in the art to which the invention pertains and as may be applied to the essential features hereinbefore set forth, as fall within the scope of the invention.

I claim:

1. A process for the preparation of halogen substituted phthalic anhydride of the formula:

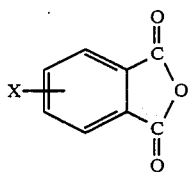

where X is a halogen, by reacting either a monohalogen substituted tetrahydrophthalic anhydride of the formula:

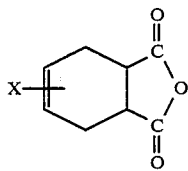

or a geminal dihalogen substituted hexahydrophthalic anhydride of the formula:

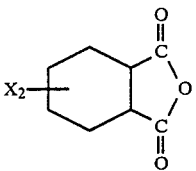

in vapor phase, admixed with air and with activated carbon as catalyst at a temperature of 200°–400° C.

2. The process according to claim 1, for the preparation of 4-chlorophthalic anhydride by reacting 4-chlorotetrahydrophthalic anhydride.

3. The process according to claim 1, for the preparation of 3-chlorophthalic anhydride by reacting 3-chlorotetrahydrophthalic anhydride.

4. A process according to claim 1 for the preparation of 4-fluorophthalic anhydride by reacting 4-fluorotetrahydrophthalic anhydride.

5. A process according to claim 1, for the preparation of 4-bromophthalic anhydride by reacting 4-bromotetrahydrophthalic anhydride.

6. A process according to claim 1, for the preparation of 4-fluorophthalic anhydride by reacting 4,4-difluorohexahydrophthalic anhydride.

7. A process according to claim 1 wherein the reaction is conducted in the range 200°–325° C.

8. A process for the preparation of a halogen substituted phthalic anhydride of the formula:

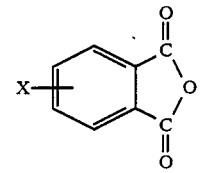

where X is a halogen, by reacting a halogen substituted tetrahydrophthalic anhydride of the formula:

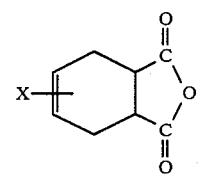

or a geminal dihalogen substituted hexahnydrophthalic anhydride of the formula:

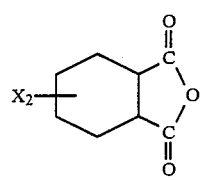

in a liquid phase, admixed with air and with an activated carbon catalyst at a temperature of 200°–300° C.

9. The process according to claim 8, for the preparation of 4-chlorophthalic anhydride by reacting 4-chlorotetrahydrophthalic anhydride.

10. The process according to claim 8, for the preparation of 3-chlorophthalic anhydride by reacting 3-chlorotetrahydrophthalic anhydride.

11. A process according to claim 8, for the preparation of 4-fluorophthalic anhydride by reacting 4-fluorotetrahydrophthalic anhydride.

12. A process according to claim 8, for the preparation of 4-bromophthalic anhydride by reacting 4-bromotetrahydrophthalic anhydride.

13. A process according to claim 8 for the preparation of 4-fluorophthalic anhydride by reacting 4,4-difluorohexahydrophthalic anhydride.

14. A process of claim 8, wherein the reaction is conducted in the range 200°–250° C.

* * * * *